(12) United States Patent
Evans et al.

(10) Patent No.: US 6,677,311 B1
(45) Date of Patent: Jan. 13, 2004

(54) INDUCIBLE HSV-TK IN TRANSFORMED CELL POPULATIONS

(75) Inventors: Ronald M. Evans, La Jolla, CA (US); Emiliana Borrelli, Strasbourg Cedex (FR); Richard Alan Heyman, Encinitas, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 1,562 days.

(21) Appl. No.: 08/464,271

(22) Filed: Jun. 5, 1995

Related U.S. Application Data (63) Continuation of application No. 08/161,203, filed on Dec. 1, 1993, now abandoned, which is a continuation of application No. 07/633,373, filed on Dec. 21, 1990, now abandoned, which is a continuation-in-part of application No. 07/221,943, filed on Jul. 20, 1988, now abandoned.

(51) Int. Cl.$^7$ .......................... A01N 43/04; A61K 31/70
(52) U.S. Cl. ............................... 514/44; 800/25
(58) Field of Search .................. 514/44; 424/93.6, 424/93.2, 93.21

(56) References Cited

PUBLICATIONS

Kappel et al (1992) Current Opinion Biotech 3, 548–553, 1992.*
Muller (1994) Pharmac. Ther. 63, 199–207, 1992.*
Ledley (1987). J. Pediatrics 110, 1–8, 1987.*
Culver et al (1992) Science 256, 1550–1552, 1992.*
Moolten (1986) Cancer Research 46, 5276–5281, 1992.*
Palmiter et al (1987) Cell 50, 435–443, 1987.*
Moolten et al (1986) Canc. Res. 46, 5276–5281.*
Palmiter (1987) Cell 50, 435–443.*
Culver et al (1992) Science 256, 1550–1552.*
Palmiter et al (1987) Cell 50, 435–443.*
Brinster et al., "Somatic Expression of Herpes Thymidine Kinase in Mice following Injection of a Fusion Gene into Eggs", Cell vol. 27:223–231 (1981).
Palmiter et al., "Differential Regulation of Metallothionein–Thymidine Kinase Fusion Genes in Transgenic Mice and Their Offspring", Cell vol. 29:701–710 (1982).
Palmiter and Brinster, "Transgenic Mice", Cell vol. 41:343–345 (1985).
Ross and Solier, "Glucocorticoid regulation of mouse mammary tumor virus sequences in transgenic mice", Proc. Natl. Acad. Sci. USA vol. 82:5880–5884 (1985).
Moolten, Tumor Chemosensitivity Conferred by Inserted Herpes Thymidine Kinase Genes: Paradigm for a Prospective Cancer Control Strategy, Cancer Research vol. 46:5276–5281 (1986).
Wilmut et al., "A revolution in animal breeding", New Scientist, pp. 56–59 (Jul. 7, 1988).
Hogan and Lyons, "Gene targeting; Getting nearer the mark", Nature vol. 336:304–305 (1988).
Mansour et al., "Disruption of the proto–oncogene int–2 in mouse embryo–derived stem cells: a general strategy for targeting mutations to non–selectable genes", Nature vol. 336:348–352 (1988).
Borrelli et al., "Targeting of an inducible toxic phenotype in animal cells", Proc. Natl. Acad. Sci. USA vol. 85:7572–7576 (1988).
Heyman et al., "Thymidine kinase obliteration: Creation of transgenic mice with controlled immune deficiency", Proc. Natl. Acad. Sci. USA vol. 86:2698–2702 (1989).
Borrelli et al., "Transgenic mice with inducible dwarfism", Nature vol. 339:538–541 (1989).
Capecchi, "Altering the Genome by Homologous Recombination", Science vol. 224:1288–1292 (1989).
Moolten et al., "Lymphoma Regression Induced by Ganciclovir in Mice Bearing a Herpes Thymidine Kinase Transgene", Human Gene Therapy vol. 1:125–134 (1990).

* cited by examiner

*Primary Examiner*—Deborah Crouch
(74) *Attorney, Agent, or Firm*—Stephen E. Reiter; Foley & Lardner (57) ABSTRACT

The present invention discloses a new selective method for inducibly and genetically ablating specific cell lineages in transgenic cell populations, e.g., in transgenic animals. The new method, which permits the production of stable transgenic perigees, and thus can be used at various stages of development of a transgenic cell population, allows both the timing and the degree of cellular ablation to be controlled. As a result the method can be used for a variety of therapeutic applications, as well as to study cell lineages and organogenesis, plus the capacity that residual stem cells have for regeneration.

18 Claims, 3 Drawing Sheets

INDUCIBLE HSV-TK IN TRANSFORMED CELL POPULATIONS

PRIOR APPLICATION

This application is a continuation-in-part of U.S. Ser. No. 07/221,943, filed Jul. 20, 1988, now pending, the contents of which are hereby incorporated by reference in their entirety.

This application is a continuation of application U.S. Ser. No. 08/161,203, filed Dec. 1, 1993 now abandoned, which is a continuation us U.S. Ser. No. 07/633,373, filed Dec. 21, 1990 now abandoned, which is a continuation-in-part of U.S. Ser. No. 07/221,943, filed Jun. 20, 1991 now abandoned, the entire contents of which are hereby incorporated by reference herein.

ACKNOWLEDGEMENT

This invention was made with Government support under Grant Nos. CA 09370 and GM 26444 awarded by the National Institutes of Health. The Government has certain rights in the invention.

TECHNICAL FIELD

The present invention relates to transgenic cell populations, e.g., transgenic cell lines and transgenic animals. More particularly, the invention relates to negative selection methods, chimeric gene constructs useful therefor, methods for establishing stable transgenic cell populations and then selectively ablating (i.e., negatively selecting for) specific cell types and/or cell lineages in such transgenic cell populations at desired stages of development or differentiation.

BACKGROUND

Positive selection procedures or negative selection procedures can be used to differentiate various cell types of a given cell population. In a positive selection situation, cells having desirable properties have one or more growth and/or maintenance advantages over cells which do not have such properties. The cells having such desirable properties outcompete the remaining cells in the cell population, and eventually overtake the remaining cells in the population. Thus, the ultimate cell population is determined, in large part, by specific features possessed by the surviving cells (but which features were not possessed by the cells which were eliminated).

In contrast, negative selection involves removing from a cell population (or destroying) those cells which do not have the specific features desired for the ultimate cell population. Thus, in the negative selection situation, the ultimate cell population is determined by one or more specific features possessed by the cells which are no longer a part of the surviving cell population.

While positive selection techniques have found widespread applicability in the field of biology, negative selection techniques have been less widely used.

The ability to more broadly apply negative selection techniques to biological systems would make possible a variety of therapeutic, prophylactic and research applications of such techniques.

For example, inadequate selectivity currently severely limits the potential efficacy of most cancer chemotherapy. Inadequate selectivity also limits the therapeutic use of many traditional chemicals, due to the likelihood of undesirable side-effects upon administration of the therapeutic agent in dose levels effective to impart the desired therapeutic effect.

Since most chemotherapeutic agents target the proliferative functions in neoplastic cells, the dosage levels of such agents must generally be limited to suboptimal levels to avoid unacceptable toxicity to normal stem cells, whose proliferation sustains vital hematopoietic and epithelial tissues. It would, therefore, be desirable to be able to selectively direct the effects of the therapeutic agent to the affected cell population, and not to the total cell population indiscriminately.

Another area where it would be desirable to be able to selectively direct the effects of treating agents is in the study of critical events in development and differentiation. For example, a major problem in the study of vertebrate development is the absence of a genetic approach for the study of such critical events in cell lineage development and differentiation. Various attempts have been made, using both mechanical and chemical methods, to specifically eliminate one cell type in a living organism. Although some success has been achieved, the complex structure of the vertebrate system has not allowed selective destruction of a single cell type to be accomplished employing prior art methods.

Recently, Palmiter, et al., in *Cell*, 50:435–443 (1987) demonstrated that transgenic mice lacking normal pancreas function could be created when fertilized mouse eggs were microinjected with a vector construct in which the elastase I promoter/enhancer was fused to a gene coding for a toxic gene product (the diphtheria toxin A polypeptide). These investigators report that some of the transgenic mice had no pancreas, while others had a small rudimentary organ which resembled an embryonic pancreas. Based on these observations, the authors suggest that the difference in development of the transgenic pancreas probably reflects differential timing of expression of the diphtheria toxin A polypeptide, in individual mice.

Breitman, et al., in *Science*, 238:1563–1565 (1987), have also demonstrated that the mouse gamma 2-crystallin promoter can be used to direct expression of the toxic gene product, diphtheria toxin A, in eye lens tissues in transgenic mice. Thus, Breitman et al. report the generation of a line of mice in which embryonic fiber cells within the lens have been genetically ablated.

Unfortunately, one problem with genetic ablation of a cell line during embryonic life is that expression of some toxin genes may be lethal to the early embryo or sufficiently toxic to prevent establishment of a stable transgenic pedigree. In addition, in order to study cell lineages, e.g., cells of the immune system, it would be useful to be able to control not only the timing, but also the degree of cellular ablation.

The ability to regulate cell ablation would make possible (1) the development of animal models mimicking various disease states, (2) treatment of various disease states, and (3) the controlled elimination from a cell population (e.g., a subject) of a cell line capable of providing to the subject a desirable component (as an exogenous gene product), once the need for such a component no longer exists, or once the subject achieves the ability to produce sufficient quantities of such component as an endogenous product.

There is, therefore a need for improved genetic ablation methods (i.e., negative selection methods) that will allow controlled manifestation of a toxic phenotype in transgenic cell populations. An improved negative selection (i.e., genetic ablation) method should permit the generation of transgenic cell populations, and it would preferably be inducible, so that the treatment of the transgenic cell population can be carried out when desired, e.g., for an intact organism, when such organism is in its embryonic and developing states, or when it is mature. Furthermore, the improved method should allow the extent or degree of the cellular ablation to be controlled. Finally, the improved method should make it possible to study the capacity a specific cell type has for regeneration. This could be done by ablating a specific cell type by treating the subject for a finite period of time, withdrawing the drug treatment, and then examining the plasticity or repopulation of the cell type system over time.

SUMMARY OF THE INVENTION

To fulfill the need for an improved negative selection (i.e., selective cell) method, the present invention discloses a new method for selectively, ablating, by genetic means, specific cell lineages in transgenic cell populations. The new negative selection method, which permits the production of stable transgenic cell populations, and thus can be used at various stages of development of a transgenic cell population, also allows both the onset and degree of cellular ablation to be controlled. Such control not only allows specific types of cells to be studied, but also enables the examination of the capacity of residual stem cells for regeneration.

Thus, the method of the invention is extremely useful, for example, for the study of immunological and neuroendocrine disorders, and possibly neurological disorders; in addition to being useful for the treatment of various disorders; and potentially useful for selectively eliminating cell line(s) which at one time served a useful purpose, but which is no longer required for normal functioning of the host organism.

DETAILED DESCRIPTION OF THE INVENTION

In accordance with the present invention, there is provided a method for the selective elimination of a specific cell-type or a specific cell line from a cell population; wherein said specific cell-type or specific cell line comprises a DNA encoding an exogenous enzyme which is expressed by said cell-type or cell line; wherein said exogenous enzyme is capable of converting a latent toxin into a substance which is toxic to said cell-type or cell line; and wherein said exogenous enzyme has substantially no effect on said cell population in the absence of said latent toxin, said method comprising:

administering said latent toxin to said cell population under conditions suitable to convert said latent toxin into said substance toxic to said cell-type or cell line; wherein said toxin is administered to said cell population in an amount sufficient to cause the death of at least a substantial portion of the cells of said cell-type or said cell line.

According to one aspect of the invention method, transgenic organisms, e.g., animals, are created that carry an exogenous structural gene (G) in their germ cell lines. According to another aspect of the present invention, transgenic animals are created that carry an exogenous structural gene (G) in their somatic cell lines.

As used herein, the phrase "exogenous structural gene" refers to a gene that: (1) is not normally found in the genomic DNA of a particular cell, or at least is not normally expressed in such a cell, and (2) encodes a structural as opposed to a regulatory protein.

Exogenous structural gene (G) codes for a "converting" enzyme (E) whose presence per se is neither beneficial nor harmful to the transgenic animal. However, due to the ability of the enzyme (E) to convert specific non-toxic substances into substances that are toxic to at least a sub-population of the transgenic cell population ("latent toxins"), the presence of enzyme (E) in cell line (C) confers a "toxic potential" on such cells.

In accordance with one embodiment of the present invention, exogenous structural gene (G) is selectively expressed, e.g., by being operatively linked to a promoter/enhancer complex that is capable of directing the expression of gene (G) in a specific cell or cell line (C) in the transgenic cell population. In accordance with another embodiment of the present invention, the latent toxin is selectively administered to that portion of the cell population which is sought to be ablated, e.g., by injection, oral administration, infusion, and the like.

As used herein, the phrase " . . . a gene (G) operatively linked to a tissue-specific promoter/enhancer complex (peC)" refers to a construct wherein expression of the gene (G) will be controlled by the action of the promoter, the enhancer, and possibly trans-acting factors related thereto.

Promoters useful in the practice of the present invention are regulatory elements that are "turned on" or otherwise activated by specific trans-acting factor(s).

Promoters contemplated for use in the practice of the present invention are typically selected from mammalian promoters or viral promoters. Exemplary mammalian promoters include growth hormone, prolactin, insulin, β-globulin, and the like. Exemplary viral promoters include Rous sarcoma virus, cytomegalovirus, and the like.

Examples of tissue-specific promoters contemplated for use in the practice of the present invention include, but are not limited to, the immunoglobulin promoter which is specific for B cells; the T4 promoter which is specific for T4 cells (a certain sub-population of the T lymphocytes that interact with targets bearing Class II major histocompatibility complex molecules); the T8 promoter which is specific for the sub-population of T lymphocytes that contains the majority of cytotoxic and suppressor cells (T8 cells interact with targets expressing Class I major histocompatibility complex molecules); the interleukin-2 receptor promoter which is specific for the sub-population of T cells that includes subserving helper cells, suppressor cells or cytotoxic cells (the foregoing cells are important in T cell populations necessary to mount a normal T cell immune response); the T cell receptor promoter which is specific for those T lymphocytes that are necessary for normal T cell immune response; the prolactin promoter which is specific for lactotrophic cells in the pituitary; the growth hormone promoter which is specific for somatotrophic cells in the pituitary; the SCG10 promoter which is a neuronal-specific promoter expressed in primordial ganglion cells and is specific for adrenal medulla and sympathetic neuron cells; and the like.

Accordingly, to control expression of the exogenous enzyme, a strong promoter can be used if the goal is to express a large amount of the "exogenous" enzyme, while a weak promoter can be used if less expression is desired. Since a non-toxic substance must be added to transgenic cells which are expressing the exogenous enzyme before any toxic substance can be produced, the ablation method of the present invention is capable of "external" control, e.g., by regulating the timing, rate and concentration at which these latent toxins are introduced into the cell population.

As used herein, the term "enhancer" refers to cis-acting DNA sequences that can act in either orientation, and over a considerable distance, to activate transcription from a linked homologous or heterologous promoter. Known enhancers include, but are not limited to, enhancer from: Simian virus 40 (SV40), Polyoma virus, Adenovirus-2E1A protein (Ad-2 E1Ah), Moloney sarcoma virus, Moloney leukemia virus, Rous sarcoma virus, Feline sarcoma virus, Bovine papilloma virus, BK Virus, Lymphotropic virus (LPV), Mammary tumor virus, Herpes virus, Human cytomegalovirus, JC Virus, Immunoglobulin heavy chain (IgH), Immunoglobulin light chain (IgL), Antithrombin III, Metallothionein-IIA human, Xenopus U2, c-fos Human, and Yeast transposon 917. Tissue-specific enhancers include the IgH and LPV enhancers, both of which are active only in lymphoid cells. The SV40 enhancer and the Xenopus U1/U2 RNA gene enhancers are examples of non-tissue specific enhancers. In addition, some enhancers are inducible; that is, some DNA segments act as enhancer elements only with the aid of an exogenous trans-acting factor or "inducer".

As used herein, the phrase "a promoter/enhancer complex capable of directing expression of an exogenous structural gene (G) to cells of type (C) from animal (A)" refers to a promoter/enhancer complex that is tissue or cell specific for tissues containing cells of type (C), and which will direct expression of an operatively linked gene in such (C) cells.

Promoter/enhancer complexes presently preferred for use in the practice of the present invention include, but are not limited to, complexes of: immune-specific promoters (the immunoglobulin light chain promoter, the T4 promoter, the T8 promoter, the interleukin-2 receptor promoter, the T cell receptor promoter, and the like), skin-specific promoters, heart-specific promoters, the prolactin promoter, the growth hormone promoter, and the like; and enhancers such as the immunoglobulin heavy chain enhancer.

According to the invention method, (C) cells that express exogenous gene (G) and thus contain enzyme (E) within the transgenic cell population, when exposed to a specific latent toxin, i.e., non-toxic drug substance that enzyme (E) converts into a substance that is toxic to the cells (C), are eliminated from the original cell population. In this manner, the toxic potential of the cell (C) is actualized, thus allowing specific cell (C) types within the transgenic cell population to be negatively selected for, i.e., to be ablated. In addition, by controlling the amount of expression of gene (G) in cell (C), which can be done, for example, by linking the gene (G) to a "weak" or a "strong" tissue-specific promoter, and by controlling the rate, dose and/or timing of the exposure of cell (C) to the non-toxic drug compounds, it is possible to control the degree and timing of the resulting genetic ablation.

Cell lines contemplated for elimination employing the invention ablation method include, but are not limited to lymphoid cells (e.g., Factor IX encoding cell lines, splenocytes, thymocytes, B-cells, T-cells, T8 cells, T4 cells, or helper cells), mesenteric lymph node cells, pituitary cells, adrenal medulla cells, sympathetic neuron cells, pancreatic cells, lens cells fibroblasts and the like.

A second aspect of the invention relates to the establishment of a stable pedigree of transgenic mice that carry the thymidine kinase gene from herpes simplex virus operatively linked to a promoter/enhancer complex capable of directing expression of the thymidine kinase gene in lymphoid cells. Such lymphoid cells are then genetically ablated, to the desired degree, and at the desired stage of development, by the introduction of controlled amounts of non-toxic drug substance(s) known generically as antiherpetic nucleoside analogs. These non-toxic analogs, when phosphorylated by the herpes thymidine kinase enzyme, are converted into substances that become "toxic" once incorporated into the replicating DNA of the cell. Such incorporation impairs further DNA replication, which subsequently leads to death of the target cells.

In another aspect, the present invention relates to DNA constructs that are useful in providing inducible genetic ablation by the method of the invention. Such constructs include the herpes virus thymidine kinase (TK) gene operatively linked to a promoter/enhancer complex capable of directing expression of the herpes TK gene in specific cell types of transgenic cell populations, e.g., in embryonic or non-embryonic transgenic animals.

In still another aspect, the present invention relates to transgenic animals carrying within their germ cells or somatic cells DNA encoding the enzyme, herpes thymidine kinase, wherein the gene encoding herpes thymidine kinase is operatively linked to a promoter/enhancer complex capable of directing expression of the herpes TK gene in specific cell types in transgenic animals.

DNA encoding said exogenous structural enzyme can be introduced into the cell or cell line which one wishes to be able to controllably ablate by a variety of methods as can readily be determined by those of skill in the art. Exemplary techniques include:

infection with retroviral constructs, microinjection, or transfection.

When introducing exogenous DNA into the host cell(s), the introduction into said cell or cell line of additional DNA encoding a desired substance, as an exogenous gene product, is also contemplated; wherein the ability to eliminate said cell or cell line from the cell population is desired, e.g., once the need for such a component no longer exists, or once the subject achieves the ability to produce sufficient quantities of such a component as an endogenous product. Such additional DNA may encode a component necessary for the normal functioning of said cell, cell line or cell population. Examples of such additional DNA include the Factor IX gene, specific growth factors, enzymes and the like.

In one aspect of the present invention, there is provided a selective method for genetically ablating specific cell lineages in transgenic cell populations, e.g., in transgenic animals. The new method was developed to address the need for a genetic ablation strategy that was not only inducible and cell specific, but also controllable, at least in terms of when and to what degree the cells would be ablated. Preferably, such a strategy would include the use of "external" components that would make it easier to regulate the timing and degree of destruction of specific cells within the transgenic animal.

As used herein, "genetic ablation" and/or "negative selection" are used interchangeable and refer to removing or eliminating specific cell types in a culture of a cell population, or in a transgenic animal host by means of a DNA construct that encodes a protein whose presence per se is not toxic to the cells but which can confer upon the cells a toxic potential due to the ability of the protein to convert non-toxic substances into substances that are or will become toxic to the cells. The elimination of specific cell-type(s) or specific cell line(s) in accordance with one aspect of the present invention produces a cell population which is substantially free of cells which are not normally present in the wild-type cell population. The elimination of specific cell-type(s) or specific cell line(s), in accordance with another aspect of the present invention, produces a defined altered state in the treated subject.

Cell(s) or cell line(s) contemplated to be eliminated in accordance with the present invention can be a cell or cell line capable of providing a desirable component to a cell population, as an exogenous gene product; wherein the ability to eliminate said cell or cell line from said cell population is desired, e.g., once said population achieves the ability to produce sufficient quantities of such component as an endogenous gene product; or, the cell line to be eliminated can be a diseased cell line or a cell line predisposed to a disease state.

Normal cell(s) or cell line(s) contemplated to be eliminated in accordance with the present invention are cell(s) or cell line(s), the elimination of which would result in the creation of a defined altered state in the cell population.

As used herein, the term "cell lineage" refers to cell type(s) that give rise to cell lines, each of which develop from a single progenitor cell.

As used herein, "inducible" refers to an event which can be made to occur by means of an external stimulus. As used herein, inducible is the opposite of constitutive, or that which occurs without the aid or influence of an external stimulus; and the term "inducer" refers to an external factor, such as a hormone or a metal ion, that can influence or effect transcription of a specific gene or genes.

Since many poisons are toxic per se to cells, use of such poisons in a genetic ablation strategy negates the ability to "externally" control when cells will be destroyed, and to what degree. Because of this, we have developed a system that utilizes an exogenous enzyme (produced by expression of an exogenous gene encoding said enzyme) whose presence per se is not toxic to the cells, but at the same time is able to confer a toxic potential on the cells, e.g., is able to convert a non-toxic substance introduced into cells into a "toxic" substance that would kill or ablate the cells (also referred to herein as a "latent toxin").

Since the invention ablation system has two main components, one "internal" and the other "external" to the cells to be destroyed, selection can be controlled in several ways. For example, controlling the amount of exogenous enzyme produced within the cells provides a means for "internally" controlling the degree of ablation. The amount of enzyme produced can be regulated by controlling the expression of the exogenous gene, for example, by operatively linking the gene to a tissue-specific promoter of a certain strength. The administration of the latent toxin can also be controlled as to when, where, and how much is administered to the cell population being treated.

As used herein, the phrase " . . . introduction of a latent toxin into cell (C) at a concentration and for a period of time sufficient to elicit the desired degree of ablation due to conversion of the latent toxin to a toxic drug substance . . . " means that it is possible to regulate the destruction or elimination of the cells (C). Conversely, when administration of the latent toxin is stopped, regeneration of the affected cells (C) can begin. The extent to which regeneration approaches the normal state depends on the extent of cell destruction due to latent toxin administration and the type of cell being eliminated. In addition to the foregoing, the rate and degree of genetic ablation can be further regulated by controlling the level of expression of enzyme (E), the enzyme that converts the latent toxin to a toxic drug substance. The onset of treatment and the age of the transgenic animal, i.e., fetus, neonate or adult, can also be manipulated to study various consequences. Further, the concentration of latent toxin, the rate and duration of administration of latent toxin, and the level of enzyme (E) present in the animal will determine the degree of cellular destruction or ablation. The degree of ablation will also vary depending on the non-toxic drug substance (latent toxin) used. However, all such parameters can be determined by a skilled artisan, without undue experimentation.

As used herein, the phrase " . . . convert a non-toxic drug substance (i.e., latent toxin) into a substance having cell toxicity (toxic drug substance) . . . " refers to the ability of an enzyme (E), such as HSV1-TK, to catalyze the conversion of latent toxin materials, such as DHPG (9-[(1,3-dihydroxy-2-propoxy) methyl] guanine); ACV (acyclovir) or FIAU (1-(2-deoxy-2-fluoro-a-D-D-arabinofuranosil)-5-iodouracil), into a substance that is capable of becoming toxic to the cells.

Other enzymes which can be employed in the practice of the present invention are non-mammalian enzymes, i.e., enzymes which are not native to the host cells contemplated for the generation of a transgenic cell population.

As used herein, the term "transgenic animal" refers to an animal that contains an exogenous gene(s) (i.e., non-native or foreign gene(s) introduced by human efforts) in its genomic or chromosomal DNA, via either the germ cells or the somatic cells of the host animal. To enhance expression of this gene, or to direct expression of the gene in specific cells, the gene is operatively linked to a promoter sequence. The gene/promoter complex is then introduced into the host by suitable means, e.g., fertilized eggs can be obtained from the animal species into which the exogenous gene is to be introduced, and the gene/promoter complex introduced into a fertilized egg, e.g., by microinjection of a DNA construct containing the gene/promoter complex.

The injected, fertilized eggs are then implanted into host females which give birth to offspring, a certain percentage of which are transgenic. Since the microinjected construct is frequently integrated into chromosomal DNA, the injected DNA is retained throughout development, and passed to offspring as Mendelian traits, thereby allowing stable transgenic pedigrees to be established. Alternatively, exogenous gene(s) can be introduced into the host cells by a variety of other techniques which are readily available to those of skill in the art, e.g., by infection with retroviral constructs, or transfection.

The pathogenic effects of herpes virus infection has led to the development of nucleoside analogs that selectively block viral spread as a consequence of their metabolism by the herpes TK enzyme, but not its cellular counterpart. As used herein, "nucleoside analog" refers to a purine or pyrimidine base in combination with a sugar moiety. Such analogs are agents which selectively block the spread of herpes virus infections as a consequence of their metabolism by herpes simplex virus 1 thymidine kinase (HSV1-TK), but not its non-viral counterpart found in animal cells. Nucleoside analogs useful in the present invention include, but are not limited to, ganciclovir, also known as DHPG or 9-[(1,3-dihydroxy-2-propoxy) methyl]guanine; acyclovir, also known as acycloguanosine or 9-[(2-hydroxyethoxy)methyl] guanine; FIAU, which is the mnemonic for 1-(2-deoxy-2-fluoro-a-D-arabinofuranosil)-5-iodouracil; FMAU, which is the mnenomic for 1-(2-deoxy-2-fluoro-a-D-arabinofuranosil)-5-methyluracil; and FIAC, which is the mnemonic for 1-(2-deoxy-2-fluoro-a-D-arabinofuranosyl)-5-iodocytosine; and the like.

One such nucleoside analog, acyclovir (ACV) has demonstrated clinical efficacy for the treatment of herpes infections in humans. Furthermore, in non-infected cells, ACV, FIAU (1-(2-deoxy-2-fluoro-a-D-arabinofuranosil)-5-iodouracil) and related compounds display little cytotoxicity. For these and other reasons, the herpes simplex thymidine kinase gene and nucleoside analogs such as ACV were employed as the initial system with which to demonstrate the operability of the improved genetic ablation method of the present invention.

Initially the thymidine kinase-ACV system was tested on cells in culture. These initial experiments showed: (1) that expression of the thymidine kinase gene is required for the conversion of the nucleoside analogs to toxic precursors (see Example I); (2) that expression of the HSV1-TK gene confers upon cells a toxic potential which can be actualized by subjecting the cells to appropriate levels of nucleoside analog drugs (see Example II); and (3) that the toxicity is proportional to both the level of expression of the HSV1-TK and the concentration of ACV or FIAU to which the cells are exposed (see Example II).

The toxic effects on cultured cells observed in these initial experiments were so striking that a new series of experiments, designed to establish that the cell-specific expression of HSV1-TK gene in transgenic animals would confer the same type of drug-dependent cytotoxicity that had been observed in cultured cells, were undertaken. More specifically, using mice and cells from the immune system as test systems, the HSV1-TK gene was linked to a promoter/enhancer complex that would target expression of the thymidine kinase enzyme to B- and T-cells in transgenic mice; this chimeric fragment was then introduced into fertilized mouse eggs.

The introduction of the HSV1-TK fragment created a transgenic founder that established a stable transgenic pedigree referred to herein as the 686 pedigree. RNA analysis of a transgenic mouse from the 686 pedigree revealed transcripts corresponding to the correct TK-RNA in spleen and thymus. Furthermore, results from TK assays performed on extracts from these tissues showed that the heterologous TK protein being expressed was biologically active (See Example III).

To demonstrate the efficacy of the ablation method of the present invention in vivo, an experiment was performed in which transgenic and non-transgenic littermates were implanted subcutaneously with a miniosmotic pump that delivered an anti-herpes nucleoside analog (FIAU) to the animals at a given concentration and at a given rate. One week after the pump was implanted the animals were sacrificed. Autopsy revealed a completely normal anatomy in the control mouse, with no apparent toxic effects after one week of nucleoside analog drug treatment. In the transgenic littermates, most organs were also normal with the dramatic exception of the spleen and thymus, both of which were markedly atrophied. (See Examples III and IV.)

These initial experiments were not designed to achieve total toxicity of the target cells. However, as those skilled in the area will appreciate, more severe and even total toxicity of the target cells could be achieved by manipulating any (or all) of the several parameters which affect the degree of ablation attainable with the method of the invention. Such parameters include the amount of enzyme (E) that is expressed in targeted transgenic cells, the relative concentration of non-toxic drug substance to which the targeted cells are exposed, the time of treatment, etc. By controlling these parameters, the method of the invention, for the first time, makes it possible to progress from mild cellular degeneration to almost complete destruction of a specific cell line, thus providing the ability to (1) create valuable animal models with which to study lineage formation and cell function; (2) treat diseased individuals by the selective ablation of disease cells, and (3) selectively ablate any cell line.

Example V then demonstrates the application of the invention ablation method to cause regression of lymphomas in transgenic mice.

As used herein, the term immunological disorder includes AIDS or Acquired Immune Deficiency syndrome; the term neurological disorder is used to refer to diseases such as Alzheimer's disease, Huntington's Chorea, etc.; the term neuroendocrine disorder is used to refer to disorders of the hypothalamus, pituitary, and/or adrenals.

As those skilled in the art will also appreciate, although the efficacy of the method of the invention has been demonstrated by means of transgenic mice carrying the herpes virus thymidine kinase gene operatively linked to a lymphoid cell specific promoter/enhancer complex, other stable pedigrees can be established merely by linking a suitable enzyme gene to an appropriate tissue-specific promoter/enhancer complex. For example, to establish stable genetic pedigrees which could be used to ablate somatotrophic cells in the pituitary, the exogenous enzyme gene could be operatively linked to the growth hormone promoter/enhancer complex, and then that chimeric fragment could be introduced into fertilized eggs from appropriate laboratory animals. Use of the prolactin promoter, for example, would make it possible to ablate lactotrophic cells in the pituitary, while use of the SCG10 promoter would allow ablation of adrenal medulla and sympathetic neuron cells, etc.

The present invention is further disclosed in the following examples. Such examples are for illustrative purposes only and are not meant to limit the scope of the appended claims in any way.

EXAMPLE I

Example I shows the inhibition of plasmid replication as the result of cooperative action between the HSVl-Tk and ACV or FIAU. For additional discussion concerning the experiments described herein, see Borrelli, et al., *Proc. Natl. Acad. Sci. USA*, 85: 7572–7576 (1988).

Figure 1A:
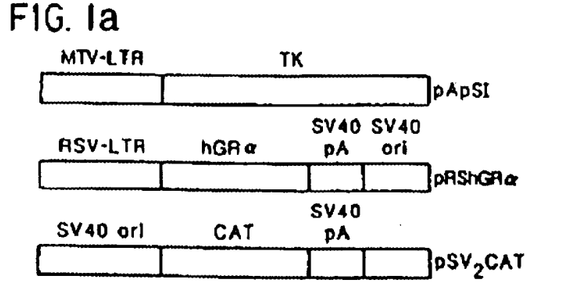
FIG. 1a is a schematic drawing of the portions of interest of plasmids pApSI, pRShGRα, and pSV$_2$CAT.
Figure 1B:
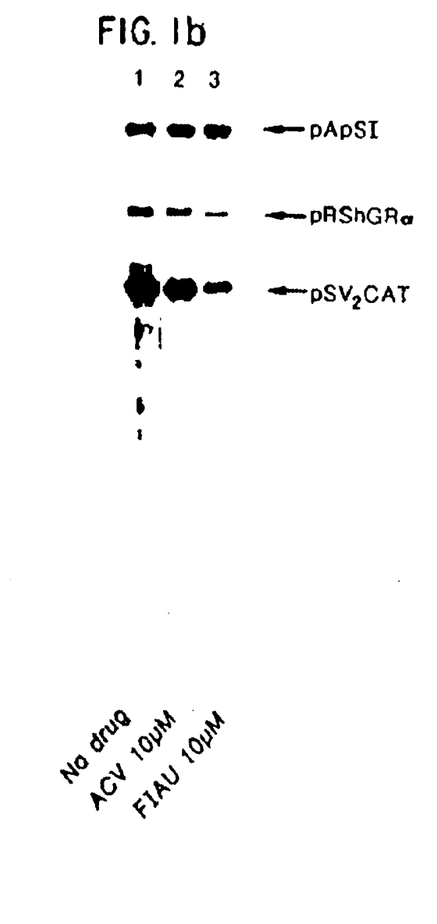
FIG. 1b is a photograph of an autoradiographed nitrocellulose filter blotted from an agarose gel of samples of plasmids pApSI, pRShGRα, and pSV2CAT grown in the presence of the nucleoside analog drugs, ACV and FIAU.
Figure 1C:
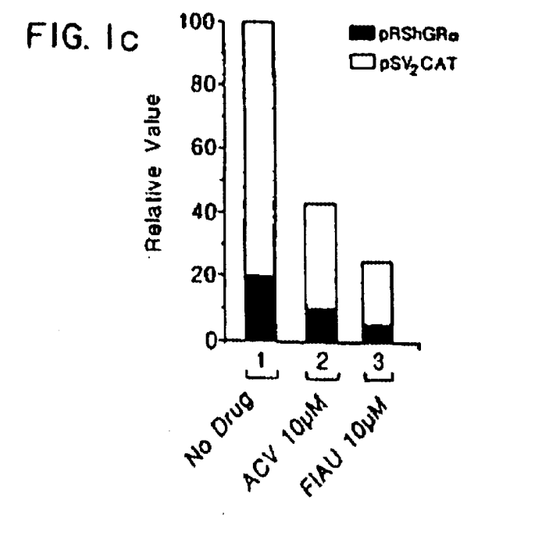
FIG. 1c is a schematic drawing of the response of plasmids pRShGRα and pSV$_2$CAT to the presence of the nucleoside analog drugs, ACV and FIAU.
Figure 2A:
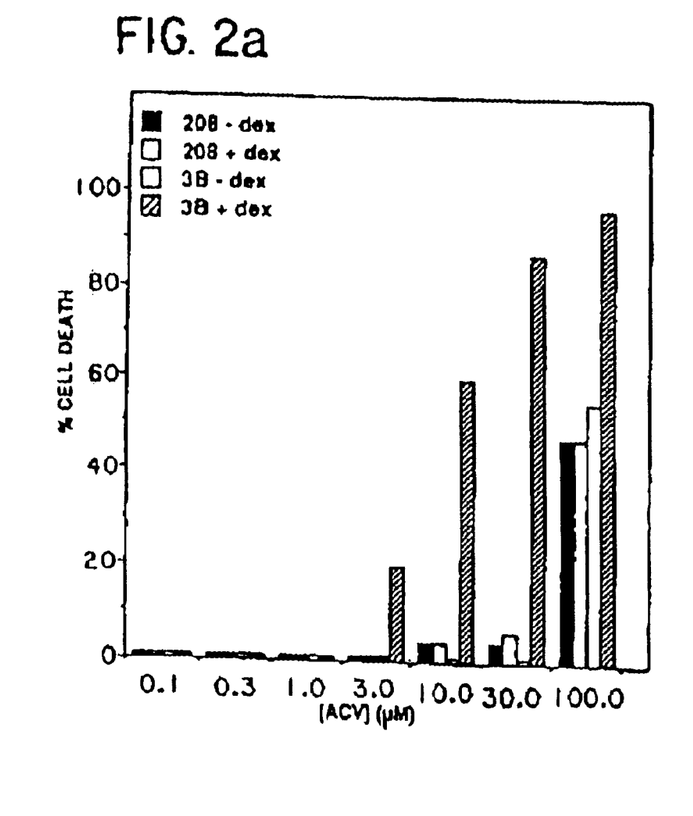
FIG. 2 comprises two graphs that demonstrate the toxic effect on the growth of 208 and 3B cells of: (a) ACV, and (b) FIAU.
Figure 2B:
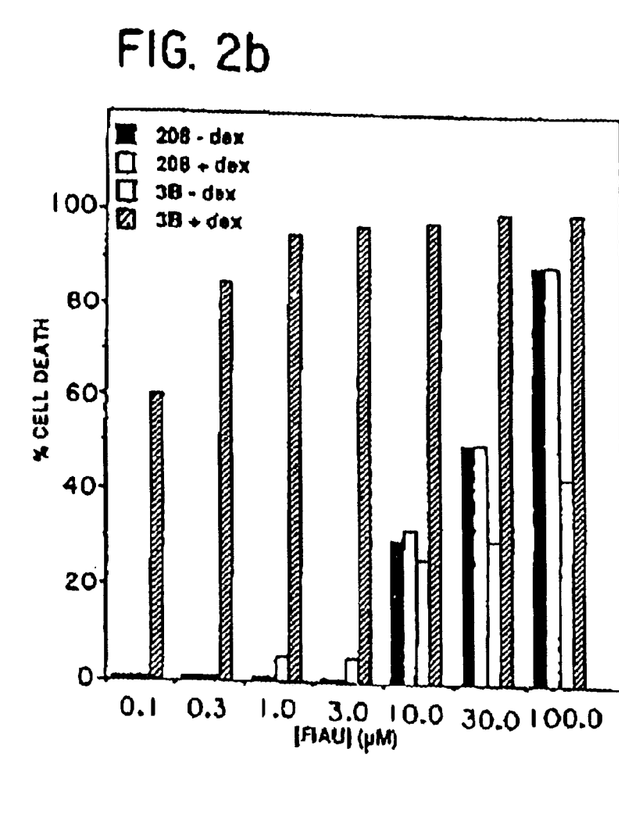

The possibility was tested that HSVI-TK expressed from a transfected plasmid could metabolize anti-herpetic nucleosides to substrates capable of being metabolized by a cellular DNA polymerase. In principle, the incorporation of these activated drugs should lead to a net decrease in cellular DNA replication. Accordingly, a plasmid capable of replicating in COS cells [monkey kidney cells which express T antigen (Tag); See Gluzman, Y. in *Cell*, 23:175–182 (1981)], namely pSV2CAT (See FIG. 1a; a plasmid that contains the Simian virus 40 promoter region linked to the chloramphenicol acetyltransferase (CAT) gene; See Gorman, et al. in *Mol. Cell. Biol.*, 2:1044–1051(1982)) was cotransfected with a plasmid, pApSI (a plasmid that contains the mouse mammary tumor virus long terminal repeat (MTV-LTR) linked to the HSV1-TK gene; See Chandler, et al., in *Cell*, 33:489–499 (1983)), expressing HSV1-TK gene under the control of the glucocorticoid inducible promoter of the mouse mammary tumor virus (MTV) (see FIG. 1a). Here, the expression of TK is dependent on both the presence of glucocorticoids, such as the synthetic dexamethasone (Dex), and the glucocorticoid receptor which activate the MTV-promoter in the presence of Dex. For this reason, a human glucocorticoid receptor (hGR) expression vector, PRShGR' (a human glucocorticoid receptor (hGR) expression vector that contains the Rous sarcoma virus long terminal repeat (RSV-LTR) linked to the human glucocorticoid receptor; See Giguere, et al., in *Cell*, 46:645–652 (1986)), was also cotransfected to insure high levels of this transacting factor. PRShGR' itself contains the origin of replication of SV40 and therefore is able to replicate in COS cells.

Semi-confluent COS cells were cotransfected by the calcium phosphate technique (See Graham, F. L. and van der Eb, A. J., *Virology*, 52:456–467 (1973) with 1 $\mu$g of pSV2CAT, 5 $\mu$g of pApS1 and 1 $\mu$g of pRShGR' and analyzed 36 hours later. The effect of ACV or FIAU on the replication of pSV2CAT was monitored by the reduction in the number of molecules of this plasmid as compared to a similar experiment conducted in the absence of these drugs. The cells were grown in Dulbecco media containing 5% FCS. Before each experiment, Dex, at a concentration of $10^{-7}$ M, was added. Where the nucleoside analogs were tested, either ACV or FIAU was added to the media at a concentration of 10 $\mu$M. When the cells were trypsinized and washed after 24 hours, and then replaced, the new media contained the same concentration of Dex and ACV or FIAU as before. 12 hours later the cells were harvested and plasmid DNA was recovered. The plasmids were recovered from the transfected cells by the method of Hirt (see *J. Mol. Biol.*, 26:365–269 (1967)). The recovered plasmid DNA was digested by BamHI, separated on a 0.8% agarose gel and then transferred onto nitrocellulose paper. The immobilized DNA was then hybridized by Southern blot analysis to a nick-translated probe containing (1) polyadenylation site of SV40 (BamHI-EcoRI fragment from SV40 position 2533–1782) or (2) pBR322.

The results of this analysis are as follows: When 10 $\mu$M ACV is added to the culture media, under the same experimental condition, the total plasmid copy number is reduced by 40% relative to no drug treatment (pSV2CAT)); the reduction is even greater (70%) when 10 $\mu$M FIAU is used (pSV2CAT). The replication of PRShGR' is also reduced in the presence of ACV and FIAU treatment. The reduction is similar to that observed with pSV2CAT. Thus, ACV and FIAU decrease, by 40% and 70% respectively, the replication of these plasmids. The plasmid pApS1 does not replicate and thus serves as an internal control. As expected, the number of copies was unchanged by any treatment. Finally, when either of the nucleoside analogs were absent or the plasmid expressing TK was absent, no reduction in the amount of pSV2CAT replication was observed, indicating that expression of thymidine kinase is required for conversion of the nucleoside analogs to toxic precursors.

EXAMPLE II

Example II illustrates the cytotoxic effect of the nucleoside analogs, ACV and FIAU, on a cell line expressing the HSV1-TK gene using a cell growth assay. For additional discussion concerning the experiments described herein, see Borrelli, et al., supra.

To examine the effect on cellular DNA replication, the rat fibroblast cell line #3B (see Pfahl, et al. *Proc. UCLA Symp. Conf. Steroid Hormone Action*, ed. Ringold, G. (Liss, N.Y.), Vol. 75:161–168 (1987) that stably expresses the glucocorticoid inducible MTV-HSV1-TK gene, was used. Addition of Dex to these cells leads to a 50-fold increase in HSV1-TK activity. The effect of the drugs on the 3B cells was compared to the one obtained on the control rat 208 fibroblast cell line (see Quade, K. (1979) in *Virology*, 98:461–465 (1979), a cell line not expressing HSV1-TK). The experiments were performed by seeding cells at low density ($3\times10^4$) in Dulbecco media containing 10% FCS. Cells were incubated with varying concentrations of drug placed in the media 12 hours after the cells were plated either in the presence or in the absence of $10^{-7}$ M Dexamethasone. After a total period of 72 hours, viable cells were recognized by Trypan blue exclusion. Cell numbers were determined with a Neubauer Hemocytometer. The efficacy of the drugs was monitored as reduction in the total number of viable cells.

At low concentrations of ACV ranging from 0.1 to 1.0 $\mu$M, no effect of the drug was observed. ACV at 3.0 $\mu$M appeared to be slightly toxic (20% cell death) but only to 3B cells, in the presence of Dex. Its toxicity to 3B in the presence of Dex was greater at higher concentrations: at 10 $\mu$M, 60% cell death was observed, and at 100 $\mu$M, 98% cell death. At 100 $\mu$M, non-specific toxicity of ACV that was independent of the presence or absence of Dex was observed. When FIAU was used, similar but more dramatic cytotoxic effects were observed.

Remarkably, concentrations as low as 0.1 $\mu$M reduced viability by more than 60% and at 3.0 $\mu$M, 98% cell death was achieved in the absence of severe non-specific toxicity. Thus, both drugs could reduce cell viability at doses that were apparently not harmful to the 208 cells. These results indicate that the expression of the HSV1-TK gene confers upon cells a toxic potential which can be revealed by the addition of appropriate levels of drugs.

EXAMPLE III

Example III shows specific cell-killing in transgenic mice. For additional discussion concerning the experiments described herein, see Borrelli, et al., supra, and Heyman, et al., *Proc. Natl. Acad. Sci. USA*, 86:2698–2702 (1989).

Figure 3A:
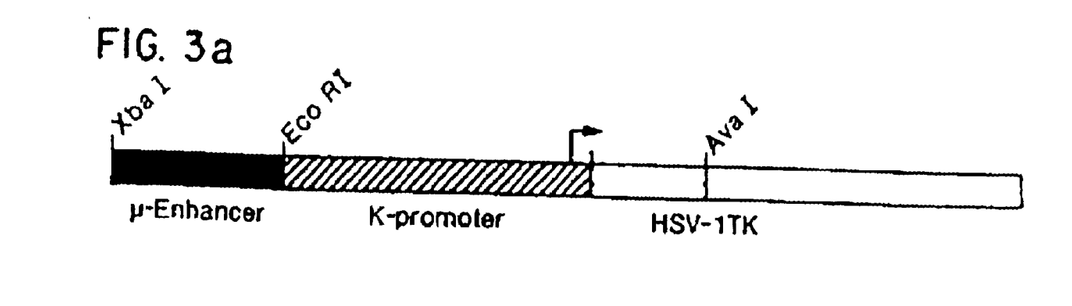
FIG. 3a is a schematic drawing which shows the structure of the KHTK plasmid.
Figure 3B:
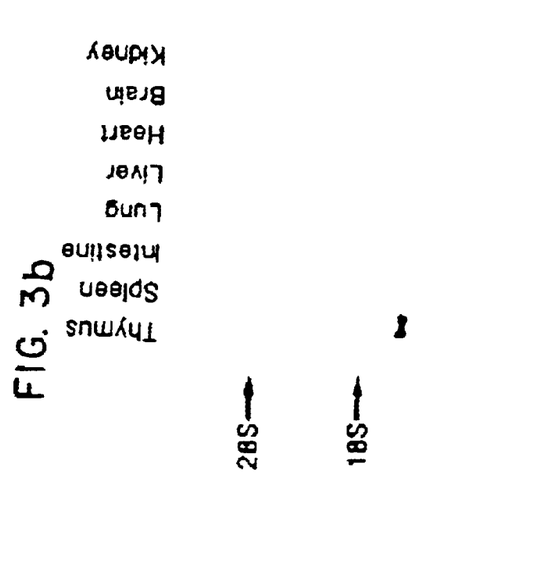
FIG. 3b is a photograph of an autoradiographed nitrocellulose filter blotted from an agarose gel, which shows a Northern blot analysis of the expression of HSV1-TK mRNA in transgenic mice.

To establish whether the cell-specific expression of HSV1-TK gene in transgenic mice would confer drug-dependent cytotoxicity as observed in cultured cells, the immune system was chosen as a model to examine the consequences of HSV1-TK gene expression. Accordingly, the plasmid pKHTK (containing the immunoglobulin heavy chain enhancer fused to the HSV1-TK gene (see Queen, C. and Baltimore, D. in *Cell*, 33:741–748 (1983)) was constructed. The KHTK plasmid is derived from pKCATH (see Victor-Garcia, et al., *Nature*, 322:383–385 (1986)) in which the CAT gene was substituted with the HSV1-TK gene. Heavy lines in FIG. 3a denote a 682 bp XbaI-EcoRI fragment of the γ-heavy chain enhancer linked to a 1.1 kb fragment of the κ-light chain promoter (hatched box) directing the transcription of a 1.5 kb fragment of the HSV1-TK gene (open box) from position +2 relative to the TK transcription start site to 236 bp downstream of the TK polydenylation site. This promoter-enhancer combination has been previously shown, in vitro, to be efficient in insuring high level expression of a reporter gene in a myeloma cell line. The KHTK fragment (see FIG. 3a) was injected into fertilized mouse eggs, giving rise to a transgenic founder that established the 686 pedigree. RNA analysis of a transgenic mouse from that line revealed transcripts corresponding to the correct TK RNA in spleen and thymus. RNA analysis was carried out as follows:

Total RNA was isolated from various tissues using the LiC1 and urea method (see Auffray, C. and Rougeon, F. *Eur. J. Biochem.*, 107:303–314 (1980), separated on 1% agarose-formaldehyde gel, transferred to nitrocellulose and hybridized by Northern blot analysis under stringent conditions using the entire HSV1-TK gene as a probe. 20 $\mu$g of total RNA was used in all lanes. Migration of the ribosomal RNAs was used as size markers. The filter was autoradiographed at $-70°$ C. with an intensifying screen for 24 hours. The resulting gel is reproduced in FIG. 3b.

Although the expression of the heavy chain enhancer-light chain promoter, in vitro, is preferential to B-cells, in transgenics the presence of the HSV1-TK in the thymus indicates that this hybrid promoter is also active in the T-cell lineage. Very low level of expression of the transgene could be observed in other tissues including liver, intestine, lung and brain following long exposure of the blot. The expression in lung and intestine may result from the presence of lymph nodes in these tissues while the significance of TK transcripts in liver and brain is unclear.

To further verify the location of the transcription start site in the transgenic tissues, an S1 analysis of the HSV1-TK MRNA in transgenic mice was performed as follows. 10 $\mu$g of total RNA from different tissues was hybridized with a double strand probe (see, Maniatis, T., Fritsh, E. F. and Sambrook, J., *Molecular Cloning*, (Cold Spring Harbor Laboratory, N.Y. 1982). spanning the region bounded by the AvaI site (+350) in the TK gene to the EcoRI site (–1100) indicated in FIG. 3a. After S1 nuclease treatment, the protected fragment, corresponding to RNA transcribed from the K light chain promoter, was 380 nucleotides in length, which is in agreement with the expected size. Si analysis reveals a correct initiation of transcription from the hybrid promoter in the same tissues already shown to contain detectable levels of TK RNA by Northern analysis. See FIG. 3a.

Furthermore, to test if the protein was biologically active, a TK assay [See Fyfe et al., *J. Biol. Chem.* 253:8721–8727 (1978)] was performed on extracts from these tissues. The results show a detectable enzyme activity only in thymus and spleen. To evaluate the efficacy of the system in vivo, an experiment was performed in which transgenic and non-transgenic littermates were implanted subcutaneously with a miniosmotic pump (model 2002, Alzet, Alza Corp., Palo Alto, Calif.). Transgenic and nontransgenic littermates were then treated for one week with a 50 mg/ml solution of FIAU in PBS released by the Miniosmotic pump. FIAU was chosen because it was most efficient in blocking the DNA replication in vitro. The dose was calculated to obtain serum levels of the drug shown to be effective in cell culture. The animals were sacrificed one week after the pump was implanted. Autopsy revealed a completely normal anatomy in the control mouse, with no apparent toxic effects after one week of FIAU treatment. In the transgenic mouse, most organs were also normal with the dramatic exception of the spleen and thymus which were visually atrophied. This was confirmed by weight and cytometric analysis revealing a reduction of 83% of the cell number in the thymus and 57% reduction in the spleen.

EXAMPLE IV

Example IV shows specific cell-killing in transgenic mice. For additional discussion concerning the experiments described herein, see Heyman et al., supra.

Figure 3C:
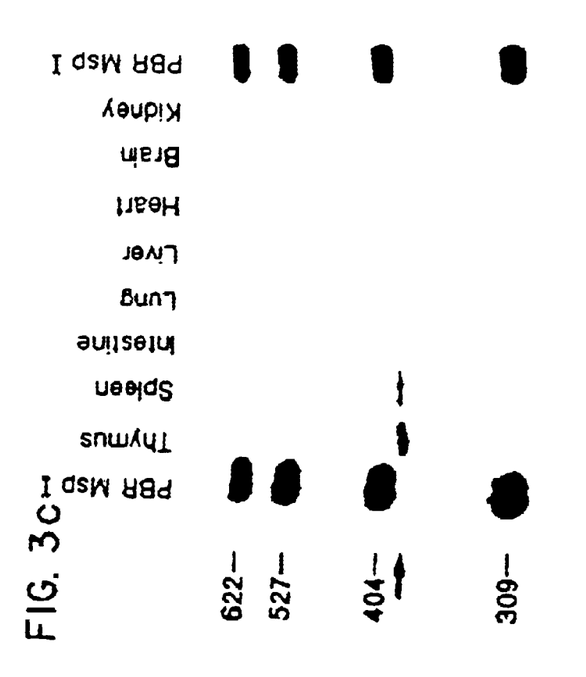
FIG. 3c is a photograph of an autoradiographed nitrocellulose filter blotted from an agarose gel, which shows an S1 nuclease analysis of the HSV1-TK MRNA in transgenic mice.

Transgenic mice were created harboring a construction consisting of the mouse immunoglobulin $\mu$ heavy chain enhancer and the $\kappa$ light chain promoter fused to the HSV-1-tk gene (FIG. 3) Twelve founder lines containing this transgene (referred to as KHTK) were generated. To verify that expression in these lines was limited to a restricted set of tissues, HSV-1-tk enzyme activity was assayed in tissue extracts from transgenic mice and their nontransgenic litter mates. Table 1 summarizes HSV-1-tk activity in various tissues from the founder lines, 552 and 563.

TABLE 1

Tissue distribution of HSV-1-tk enzyme activity in KHTK mice.

| Tissue | HSV-1-tk activity, pmol per min per mg of protein | |
|---|---|---|
| | Line 552 | Line 563 |
| Spleen | 1.1 | 2.9 |
| thymus | 5.5 | 5.7 |
| Bone Marrow | 1.0 | 0.6 |
| Lymph node | 1.6 | 1.0 |
| Cerebral cortex | <0.03 | 0.4 |
| Liver | <0.03 | <0.03 |
| Kidney | <0.03 | <0.03 |
| Ovaries | <0.03 | <0.03 |
| Heart | <0.03 | <0.03 |

Tissue extracts from KHTK mice were prepared and assayed for HSV-1-tk activity. Data are means of three determinations.

Enzyme activity was present in spleen, thymus, bone marrow, and mesenteric lymph nodes of both lines. With the exception of the cerebral cortex in founder line 563, no enzyme activity was observed in other tissues assayed. There was no detectable enzyme activity in nontransgenic litter mates. This pattern demonstrates that HSV-1-tk expression is relatively lymphoid-specific, although not necessarily restricted to B-cell lineages.

The pattern of Cell Ablation in Tissues Expressing HSV-1-tk. Transgenic mice from founder line 563 and their non-transgenic litter mates were treated with the nucleoside analog GCV for 1 week by using a miniosmotic pump. This delivery achieves a steady-state serum concentration of 1–5 $\mu$M within 24 hr (as determined by HPLC). The concentration of GCV in all tissues assayed was comparable to this value. A separate control group was implanted with a miniosmotic pump containing isotonic phosphate-buffered saline (PBS). After 7 days of drug treatment, macroscopic examination of transgenic mice treated with GCV (n=22) revealed a severe atrophy of the thymus, spleen, and mesenteric lymph nodes. The wet weights of the spleen and thymus were reduced to 15% of control and wet weights of lymph nodes were reduced to 20% of control. All nonlymphoid tissues were normal. Analysis of nontransgenic mice treated with GCV (n=16) revealed no apparent pathology and wet weights of the internal organs were normal.

Consistent with the decreased organ weight, the number of cells in the spleen, bone marrow, and thymus of GCV-treated transgenic mice decreased to 15%, 15%, and 2% of control values, respectively. In contrast, cell counts of lymphoid tissues of nontransgenic mice treated with GCV remained unchanged from the PBS-treated group. GCV treatment, therefore, selectively destroys tissues expressing HSV-1-tk with no apparent effect on tissues that do not express this enzyme.

The pathologic effect of GCV treatment was further evaluated by histological analysis. Serial cross sections through the thymus from PBS-treated mice reveal a normal thymic structure that consists of a series of encapsulated lobules composed of a dark staining peripheral zone, the cortex, and a lighter staining central zone, the medulla. The thymus from nontransgenic mice treated with drug for 7 days appears normal. In contrast, GCV treatment of transgenic mice produced an atrophied thymus with a virtual complete absence of the cortex and a hypocellular medulla. This indicates that regions of the thymus that are known to contain the highest density of rapidly dividing thymocytes have been ablated. Additional histological analysis of spleen and mesenteric lymph nodes of transgenic and nontransgenic littermates treated with GCV revealed extensive cellular destruction only in transgenic mice.

Although the pattern of toxicity was clearly lymphoid-specific, it was not possible to evaluate the impact of GCV treatment on subpopulations of B and T cells by visual inspection. Flow cytometry was employed to analyze specific populations of B and T lymphocytes in mice subjected to various GCV treatment protocols. B lymphocytes were identified by analyzine for the markers, immunoglobulin and B220, and T lymphocytes were identified by Thy-1. After 7 days of GCV treatment, striking and different effects were observed on B and T lymphocytes in spleens of KHTK mice (FIG. 4). The most dramatic impact was on immunoglobulin and B220-positive B cells, which were reduced by a factor of 20 after GCV treatment. Cells bearing the T-cell surface marker, Thy-1, had decreased to 35% of the PBS group. Thus, although both B and T cells in the periphery were sensitive to the toxic action of GCV, B-cell lineages were more susceptible to ablation. Transgenic mice treated with PBS and nontransgenic mice treated with GCV had a normal [profile of antigenic markers, indicating that neither HSV-1-tk expression by itself nor GCV treatment alone was sufficient to achieve toxicity.

A similar analysis was used to examine the impact of GCV treatment on thymocytes expressing the T-cell surface antigens L3T4 and Lyt-2 (Table 2).

TABLE 2

Phenotype of T-cell lineages of KHTK mice after GCV treatment.

| Markers | % thymocytes | |
|---|---|---|
| | Nontransgenic | Transgenic |
| $L3T4^+$, $Lyt-2^+$ | 80 | 21 |
| $L3T4^+$, $Lyt-2^-$ | 10 | 27 |
| $L3T4^-$, $Lyt-2^+$ | 4 | 21 |
| $L3T4^-$, $Lyt-2^-$ | 5 | 30 |
| $CD3.\epsilon^+$ | 35 | 76 |
| Total cell number | $6.3 \times 10^7$ | $3.8 \times 10^6$ |

Mice of transgenic line 552 or nontransgenic littermates were treated with GCV for 5 days. The thymuses of individual mice were assayed by two-color flow cytometry and reported as a percentage of total thymocytes expressing the indicated markers. Data are typical of three experiments.

Mice were treated with GCV for 5 days and then two-color flow cytometry was performed to assess the effect of GCV treatment on double-positive, single-positive, and double-negative populations. In non-transgenic mice, 80% of cells were double-positive, 14% were single-positive, and 5% were double-negative. The composition of cells surviving GCV treatment in transgenic mice was markedly altered from that of the control population. There was a relative depletion by a factor of 4 in the double-positive $L3T4^{+, Lyt-}2^+$ population and a 3- to 5-fold increase in single-positive $L3T4^{+, Lyt-}2^-$ and $L3T4^-$, $Lyt-2^+$ cells. There was also an increase in the percentage of cells expressing T-cell receptor complex-associated molecule $CD3.\epsilon$. These data imply a relative enrichment for more mature cells typical of populations in the thymic medulla and are in agreement with the histological data. There was also a 6-fold increase in $L3T4^-$, $Lyt-2^-$ cells. Based on the distribution of other markers, the $L3T4^-$, $Lyt-2^-$ populations in the thymus of drug-treated mice is heterogeneous and includes cells with phenotypes that have been associated with early thymocyte progenitors as well as heat-stable antigen-negative $CD3^+$ cells, which do not have demonstrable progenitor activity. Two-color flow analysis indicates that $L3T4^-$, $Lyt-2^-$ cells comprise both phenotypic classes. It should be pointed out that, although single-positive and $CD3^+$ cells are relatively enriched in the thymus of drug-treated animals (i.e., percentage), in terms of absolute cell number all thymic lineages are ablated in drug-treated transgenic animals.

Recovery of the Lymphoid System following GCV Treatment. One potential advantage of the conditional ablation method is the ability to remove the drug and evaluate the regenerative capabilities of the affected cell lineages. Repopulation of specific thymocyte lineages in KHTK mice was examined by subjecting mice to a severe ablation of lymphoid tissues followed by a recovery period. Accordingly, one group of animals was treated with GCV or PBS for 7 days followed by a 7-day recovery period. All groups were assayed simultaneously for the total number of thymocytes and the presence of specific antigenic markers. Transgenic mice treated with PBS had $1.1 \times 10^8$ thymocytes, whereas, after 7 days of GCV treatment, >99% of the thymocyte population was depleted. After 7 days of recovery, the total number of cells increased by 60-fold to nearly 50% of the PBS-treated control group. To characterize specific populations of thymocytes in the depleted and recovery thymus, one-color flow cytometry was performed. GCV treatment of transgenic mice resulted in a large decrease in $L3T4^+$ and $Lyt-2^+$ cells. However, after a 7-day recovery, both $L3T4^+$ and Lyt-2 populations were very similar to control values, indicating that sufficient residual stem cells remained in the thymus and/or bone marrow to repopulate these lineages. Nontransgenic mice treated with GCV had the same percentage of $L3T4^+$ and $Lyt-2^+$ thymocytes as PBS-treated animals. The phenotype of the recovering nontransgenic animals was the same as the control group, indicating that GCV treatment had no non-specific effects on T-cell lineages.

Additional analysis of the conditional cell ablation method of the present invention has been performed examining the growth hormone-containing cells in the pituitary, with similar results. See Borrelli, et al., in *Nature*, 339:538–541 (1989).

In contrast to the suggestions of prior art applications of the herpes simplex thymidine kinase gene, we have found that the invention method (employing TK plus latent toxins) can successfully be carried out employing both thymidine kinase competent, as well as thymidine kinase deficient host cells. Prior to the present work, it has been taught in the art to use only thymidine kinase deficient host cells when transfecting cells with the herpes simplex thymidine kinase gene. The ability to use thymidine kinase competent cells greatly expands the applicability of the invention method. Thus, a wide range of host cells are contemplated for use in the practice of the present invention.

EXAMPLE V

Example V shows regression of lymphomas in transgenic mice by treatment with the latent toxin, ganciclovir. For additional discussion concerning the experiments described herein, see Moolten, et al., *Human Gene Therapy*, 1:125–134 (1990).

Lymphomas were induced by injecting 5 to 6 week old transgenic mice (generated as described in Example III) intravenously with 0.5 ml of cell-free medium from confluent cultures of 1806-6 cells grown in Dulbecco's medium containing 7% calf serum and 7% fetal bovine serum (Green et al., 1987). These cells produce helper-free Abelson leukemia virus, which induces monoclonal lymphomas principally of the fre-B cell type. The virus encodes a transforming protein but is defective and therefore incapable of replicating or of encoding retroviral antigens in the lymphoma cells it helps to generate. Starting 14 days after virus administration, the mice were palpated daily for lymphomas. These were detectable as small, firm, bilateral nodules in the inguinal region, representing enlarged inguinal lymph nodes. In most cases, the presence of the tumors could be suspected 1–2 days preceding a definitive diagnosis, but the latter was made only after daily palpation confirmed the presence and the growing nature of the enlarged nodes. In the litters used, more than 90% of the injected mice developed lymphomas.

Lymphomas were first detected 2–5 weeks after virus administration, with a median latency of 17 and 18 days for transgenic mice and their nontransgenic littermates, respectively. In untreated mice the lymphomas grew over the course of 1–3 weeks to produce massive, generalized enlargement of peripheral lymph nodes. Autopsies of mice killed at this stage revealed marked enlargement of the spleen, thymus, and mesenteric lymph nodes. Mice sacrificed when tumors first became palpable also exhibited enlargement of the spleen and visceral lymph nodes, although to a lesser degree. Thus, the lymphoma is a disseminated neoplasm at the time it is first detectable.

In initial experiments, several transgenic mice were treated with GCV for 5 days (10 doses) without precautions against infection, based on dose schedules previously found to be well tolerated in nontransgenic mice [Moolten, Cancer Res. 46:5276–5281 (1986)]. In all cases the tumors regressed and became undetectable after the fifth dose, but the mice died, usually during the second week. Autopsy revealed severe atrophy of the spleen and thymus and no visible lymph nodes; there was no evidence of lymphoma. Presuming these deaths to be due to infections consequent to the lymphoid depletion, we limited the GCV therapy to five doses for the subsequent trials reported below and instituted the short-term infection control regimen detailed above, which entailed the use of sterile cages and sterile food and water during a 21-day isolation period. These modifications eliminated all drug-related deaths.

In all of the transgenic mice treated with this GCV regimen, the lymphoma shrank. In 11 of 12 mice it became undetectable by the third day after initiation of GCV therapy (Table 3). In the remaining mouse, the regression was incomplete. In 5 of the 11 mice with complete regressions, no recurrence was detected over an observation period that extended for more than 100 days from the time of diagnosis (range 102–148 days). Three other mice exhibited late recurrences of lymphoma at 31, 55 and 81 days; their survival was substantially prolonged (47, 63 and 90 days) relative to the survival of the various control groups listed in Table 3 (median survival 8–13 days). In the remaining 3 mice with complete regressions and the 1 mouse with a partial regression, recurrent lymphoma growth was detected by visual inspection during the 21-day isolation period. The survival intervals of this group (10, 24, 34 and 39 days) represent a modest prolongation relative to the controls. It is possible that some of the mice that remained free of lymphoma were cured, since the recurrence pattern is compatible with a probability of recurrence that diminishes with time; the pattern does not, however, exclude the possibility that some degree of risk persists indefinitely. In contrast to the transgenic mice, their nontransgenic littermates and other nontransgenic controls all exhibited progressive tumor growth that was unaltered by the therapy. Although the mice listed in Table 3 has exhibited only early manifestations of lymphoma when GCV therapy was started, later stages of the disease also respond only in transgenic mice.

TABLE 3

LYMPHOMA RESPONSE TO GCV IN HSV-TK TRANSGENIC MICE AND NONTRANSGENIC MICE

| Treatment Group | GCV Therapy | Fraction of Mice with complete Regressions | Number remaining recurrence-free for >100 days | Median survival (days) of mice with recurrent or persistent lymphoma |
|---|---|---|---|---|
| HSV-TK transgenics | + | 11/12 | 5 | 39 |
| | − | 0/12 | 0 | 8 |
| Nontransgenics Line 563 littermates | + | 0/17 | 0 | 13 |
| | − | 0/12 | 0 | 10 |
| Other nontransgenics | + | 0/23 | 0 | 8 |
| | − | 0/49 | 0 | 10 |

GCV treatment was begun when lymphomas first appeared. Mice with progressive lymphoma did not appear ill until late in the course of their disease, when they became listless and exhibited a hunched posture and ruffled fur. After it was determined that death inevitably followed these preterminal symptoms, usually within 4 days, were killed animals when the symptoms first appeared rather than utilizing natural death as a survival end point; in the few cases where mice died with large tumors but without preterminal symptoms, the day of natural death was recorded as the end point. This practice introduced about 4 days of imprecision into the estimates of median survival but conforms to current humane guidelines [Medical Research Council, UK Coordinating Committee on Cancer Research: guidelines for the welfare of animals in experimental neoplasia (1988); Kallman et al., Cancer Res. 45:6541–6544 (1985)]. The transgenic mice and littermates were used from 10 litters born to 6 female line 563 transgenic mice mated to BALB/c males. The other nontransgenic controls listed comprised, in the GCV-treated group, 15 C57B1/6×BALB/c (CB6) mice $F_1$ and F2generations) and 8 CB6F1×BALB/c mice, and in the untreated group 29 CB6 ($F_1$ and $F_2$,5 CB6F1×BALB/c, and 15 BALB/c mice. Since the founder mouse of the 563 line was heterozygous for genes derived from C57B1/6 and BALB/c mice, these additional mice complemented the littermate controls by eliminating the possibility that differences between transgenic mice and their littermates were attributable not to the transgene itself but to some other endogenous gene affecting the behavior of lymphomas that differ between C57B1/6 and BALB/c mice and which by accident of integration site found itself genetically linked to the transgene.

The results of HSV enzyme assays of normal and lymphomatous tissues from transgenic mice are presented in Table 4. Enzyme activity was demonstrable in normal spleen and was present at higher levels in lymphomatous spleens and lymph nodes from untreated mice. In mice with lymphoma that recurred after therapy, 1 of the 6 lymphomas tested (detected at 81 days) also exhibited high levels of activity, but the remaining 5 mice exhibited a range of values—1.3–12.4 in spleens (mean 5.7) and 1.3–16.6 in lymph nodes (mean 5.5)—that were well below the range found in the spleens (24.8–60.0, mean 40.6) or lymph nodes (23.0–55.0, mean 35.1) of the untreated mice. Within this low range, considerable variation was observed, not only between mice but also between spleen and lymph node samples from the same mouse.

TABLE 4

HSV-TK ENZYME ACTIVITY IN TISSUES FROM TRANSGENIC MICE

|  | Spleen | Lymph Node | Cultured cells[b] | Lung[c] | Intestine[c] |
|---|---|---|---|---|---|
| Mice without lymphoma (5) | 15.1 ± 2.9 | — | — | 0.6 ± 0.2 | <0.2 |
| Mice with untreated lymphoma (8) | 40.6 ± 2.9 | 35.1 ± 3.5 | — | — | — |
| Mice with lymphoma recurrent at <21 days | 1.7 | 2.9 | <0.2 | — | — |
|  | 12.4 | 5.2 | — | — | — |
|  | 1.3 | 1.7 | — | — | — |
|  | 5.9 | 16.6 | <0.2 | — | — |
|  | 7.1 | 1.3 | <0.2 | — | — |
|  | 57.5 | 46.6 | — | — | — |

[a]The numbers of mice samples are cited in parenthesis. Results are presented as sample means ± SE, expressed as pmoles of iododeoxycytidine phosphorylated/hr.mg protein. Tissues from nontransgenic mice invariably failed to exhibit activity that exceeded background levels (<0.2 pmoles/hr.mg). A dash (—) signifies the assay was not done. Lymphomatous tissues were obtained from mice killed at the appearance of preterminal symptoms, as described in Table 3.
[b]Lymph node cells from three recurrent lymphomas were propagated in RPMI-1640 medium with 5% fetal bovine serum, antibiotics, and 5 × 10$^{-5}$M 2-mercaptoethanol. Similar attempts with other primary or recurrent lymphomas failed to yield propagable cell lines.
[c]The low level activity observed in lung is consistent with that tissue's content of lymphocytes. The intestinal samples were from the duodenum because of its lower lymphocyte content than more distal areas of intestine. Tissues found negative for expression in an earlier study included liver, kidney, heart and ovary [Heyman et al., Proc. Nat'l. Acad. Sci. USA 86:2698–2702 (1989)].

While the invention has been described with some particularity in the present specification, those of ordinary skill in the pertinent art will recognize numerous modifications and variations that are within the spirit of the invention. It is intended that such modifications and variations are also within the scope of the appended claims.

What is claimed is:

1. A method for selectively inhibiting growth or causing death of a tissue-type or cell line in an intact organism;
   wherein said tissue-type or cell line comprises endogenous thymidine kinase and further comprises DNA encoding and expressing an exogenous herpes simplex thymidine kinase enzyme that selectively converts a latent toxin into a cell toxin in said tissue-type or said specific cell line, wherein said DNA is operatively linked to a promoter specific for said tissue-type or said cell line,
   said method comprising administering to said organism an amount of said latent toxin effective to trigger generation of said cell toxin by enzymatic conversion of the latent toxin; thereby selectively inhibiting growth or causing death of at least a substantial portion of said tissue-type or cell line.

2. A method according to claim 1 wherein said cell line contributes to the germ line of said organism.

3. A method according to claim 2 wherein said DNA encoding said exogenous enzyme is introduced into the germ line of said organism by:
   infection with retroviral constructs,
   microinjection of fertilized eggs, or
   transfection.

4. A method according to claim 2 wherein additional DNA encoding an exogenous gene product is introduced into said tissue-type or cell line.

5. A method according to claim 1 wherein said cell line contributes to the somatic cells of said organism.

6. A method according to claim 1 wherein said DNA encoding said exogenous enzyme is introduced into the cell line of said organism by:
   infection with retroviral constructs,
   microinjection, or
   transfection.

7. A method according to claim 5 wherein additional DNA encoding an exogenous gene product is introduced into said tissue-type or cell line.

8. A method according to claim 1 wherein expression of said DNA encoding said exogenous enzyme is controlled by a tissue specific promoter/enhancer complex containing said tissue specific promoter operatively lined to said DNA.

9. A method according to claim 1 wherein said latent toxin is selectively administered to said tissue-type or said cell line.

10. A method according to claim 1 wherein said promoter is selected from mammalian promoters or viral promoters.

11. A method according to claim 10 wherein said mammalian promoters are selected from promoters for growth hormone, prolactin, insulin, or β-globin.

12. A method according to claim 10 wherein said viral promoters are selected from Rous sarcoma virus or cytomegalovirus promoters.

13. A method according to claim 1 wherein expression of said DNA encoding said exogenous enzyme is inducible.

14. A method according to claim 1 wherein said administering leads to substantial elimination of said tissue-type or cell line from said organism, thereby reversing a condition artificially induced in said organism.

15. A method according to claim 14 wherein said tissue-type or cell line provides a desired substance to said organism, as an exogenous gene product; wherein
   the ability to substantially eliminate said tissue-type or cell line from said organism is desired.

16. A method according to claim 14 wherein said cell line is diseased or predisposed to the occurrence of a disease state.

17. A method according to claim 1 wherein said latent toxin is an anti-herpetic nucleoside analog selected from ganciclovir, acyclovir, FIAU, FMAU or FIAC.

18. A method according to claim 1 wherein said tissue-type or cell line is transgenic, transformed, implanted, or has been otherwise induced to an abnormal state.

* * * * *

UNITED STATES PATENT AND TRADEMARK OFFICE
CERTIFICATE OF CORRECTION

PATENT NO. : 6,677,311 B1
DATED : January 13, 2004
INVENTOR(S) : Ronald M. Evans et al.

It is certified that error appears in the above-identified patent and that said Letters Patent is hereby corrected as shown below:

<u>Title page, Item [54] and Column 1, lines 1-2,</u>
Title, delete "INDUCIBLE HSV-TK IN TRANSFORMED CELL POPULATIONS" and insert -- METHOD FOR SELECTIVELY INHIBITING GROWTH OR CAUSING DEATH OF A TISSUE-TYPE OR CELL LINE IN AN INTACT ORGANISM --.

<u>Column 20,</u>
Line 15, change "claim 1" to -- claim 5 --
Line 29, change "lined" to -- linked --

Signed and Sealed this

Twenty-fifth Day of May, 2004

JON W. DUDAS
*Acting Director of the United States Patent and Trademark Office*